United States Patent
Rossignol et al.

(10) Patent No.: US 11,173,149 B2
(45) Date of Patent: Nov. 16, 2021

(54) INHIBITION OF PROTEIN DISULFIDE-ISOMERASE A3

(71) Applicant: Romark Laboratories L.C., Tampa, FL (US)

(72) Inventors: Jean-Francois Rossignol, St. Petersburg, FL (US); Maria Gabriella Santoro, Rome (IT)

(73) Assignee: Romark Laboratories L.C., Tampa, FL (US)

( * ) Notice: Subject to any disclaimer, the term of this patent is extended or adjusted under 35 U.S.C. 154(b) by 82 days.

(21) Appl. No.: 16/605,978

(22) PCT Filed: Apr. 17, 2018

(86) PCT No.: PCT/US2018/027900
§ 371 (c)(1),
(2) Date: Oct. 17, 2019

(87) PCT Pub. No.: WO2018/195035
PCT Pub. Date: Oct. 25, 2018

(65) Prior Publication Data
US 2020/0038377 A1    Feb. 6, 2020

Related U.S. Application Data

(60) Provisional application No. 62/486,616, filed on Apr. 18, 2017.

(51) Int. Cl.
*A61K 31/426* (2006.01)

(52) U.S. Cl.
CPC ........ *A61K 31/426* (2013.01); *A61K 2300/00* (2013.01)

(58) Field of Classification Search
CPC .................................................. A61K 31/426
USPC ........................................................ 514/370
See application file for complete search history.

(56) References Cited

U.S. PATENT DOCUMENTS

| | | | |
|---|---|---|---|
| 3,950,351 A | 4/1976 | Rossignol et al. |
| 5,387,598 A | 2/1995 | Rossignol |
| 5,856,348 A | 1/1999 | Rossignol |
| 5,859,038 A | 1/1999 | Rossignol |
| 5,886,013 A | 3/1999 | Rossignol |
| 5,935,591 A | 8/1999 | Rossignol et al. |
| 5,965,590 A | 10/1999 | Rossignol |
| 5,968,961 A | 10/1999 | Rossignol |
| 6,020,353 A | 2/2000 | Rossignol |
| 6,117,894 A | 9/2000 | Rossignol |
| 7,285,567 B2 | 10/2007 | Rossignol |
| 7,550,493 B2 | 6/2009 | Rossignol |
| 7,645,783 B2 | 1/2010 | Rossignol |
| 8,124,632 B2 | 2/2012 | Rossignol et al. |
| 8,524,278 B2 | 9/2013 | Rossignol et al. |
| 8,633,230 B2 | 1/2014 | Rossignol |
| 8,772,502 B2 | 7/2014 | Semple et al. |
| 8,846,727 B2 | 9/2014 | Rossignol et al. |
| 8,895,752 B2 | 11/2014 | Rossignol et al. |
| 9,023,877 B2 | 5/2015 | Rossignol et al. |
| 9,107,913 B2 | 8/2015 | Rossignol |
| 9,126,992 B2 | 9/2015 | Rossignol et al. |
| 9,351,937 B2 | 5/2016 | Rossignol et al. |
| 2007/0202496 A1 | 8/2007 | Beretta |
| 2009/0036467 A1 | 2/2009 | Rossignol et al. |
| 2012/0294831 A1 | 11/2012 | Rossignol |
| 2014/0065215 A1 | 3/2014 | Rossignol et al. |
| 2015/0250768 A1 | 9/2015 | Rossignol et al. |
| 2016/0116473 A1 | 4/2016 | Kim et al. |
| 2016/0243087 A1 | 8/2016 | Rossignol et al. |

FOREIGN PATENT DOCUMENTS

WO    WO 2006/042195 A1    4/2006

OTHER PUBLICATIONS

Belardo et al., "Synergistic Effect of Nitazoxanide with Neuramidnidase Inhibitors against Influenza A Viruses In Vitro," Antimicrob. Agents Chemother., Feb. 2015, 59(2): 1061-1069.
Bernasconi et al., "The IκB Kinaes is a Key Factor in Triggering Influenza A Virus-induced Inflammatory Cytokine Production in Airway Epithelial Cells," Journal of Biological Chemistry, Jun. 24, 2005 (online Apr. 18, 2005) 280(25):24127-24134.
Caselli et al., "Human herpesvirus 8 acute infection of endothelial cells induces monocyte chemoattractant protein 1-dependent capillary-like structure formation: role of the IKK/NF-κB pathway," Blood, Apr. 1, 2007, 109(7):2718-2726.
Di Santo et al., "Research Perspective: Potential Role of Nitazoxanide in Ovarian Cancer Treatment. Old Drug, New Purpose?", Cancers, 2013, 5:1163-1176.
Glaser et al., "Effective replication of human influenza viruses in mice lacking a major α2,6 sialyltransferase," Virus Res., Feb. 20, 2007, 126:9-18.
Hebert et al., "Glucose Trimming and Reglucosylation Determine Glycoprotein Association with Calnexin in the Endoplasmic Reticulum," Cell, May 5, 1995, 81:425-433.
Hebert et al., "In and Out of the ER: Protein Folding, Quality Control, Degradation, and Related Human Diseases," Physiol. Rev., 2007, 87:1377-1408.
Kreitzer et al., "Three-dimensional analysis of post-Golgi carrier exocytosis in epithelial cells," Nat. Cell. Biol., Jan. 27, 2003, 5:126-136.
La Frazia et al., "Antiviral activity or proteasome inhibitors in herpes simplex virus-1 infection: role of nuclear factor-κB," Antiviral Therapy, 2006, 11(3):995-1004.

(Continued)

*Primary Examiner* — Kahsay Habte
(74) *Attorney, Agent, or Firm* — Foley & Lardner LLP

(57) ABSTRACT

Provided are methods of treating a disease or condition associated with an increased level of expression of a protein disulfide-isomerase A3 (PDIA3) by administering to a subject with an increased level of expression of PDIA3 a PDIA3-inhibiting effective amount of a thiazolide compound, such as nitazoxanide or tizoxanide. Also provided are methods of screening for therapeutic agents based on PDIA3 inhibition.

Figure 1:
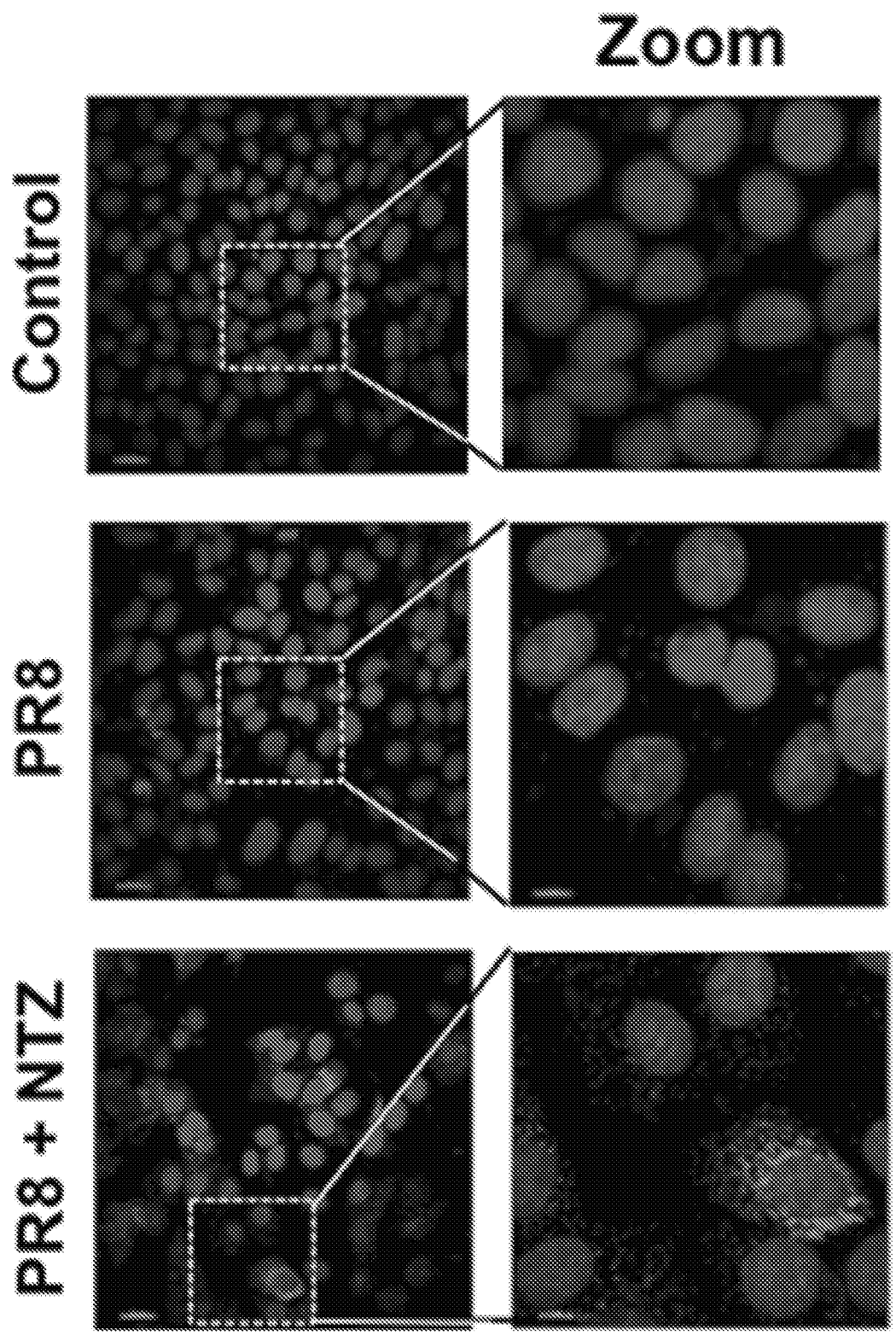

8 Claims, 8 Drawing Sheets
Specification includes a Sequence Listing.

(56) References Cited

OTHER PUBLICATIONS

Mishin et al., "Effect of Hemagglutinin Glycosylation of Influenza Virus Susceptibility to Neuraminidase Inhibitors," J. Virol., Oct. 2005, 79(19):12416-12424.

Molinari et al., "Contrasting Functions of Calreticulin and Calnexin in Glycoprotein Folding and ER Quality Control," Mol. Cell, Jan. 16, 2004, 13:125-135.

Mueller et al., "*Neospora caninum*: Functional inhibition of protein disulfide isomerase by the broad-spectrum anti-parasitic drug nitazoxanide and other thiazolides," Experimental Parasitology, 2008, 118:80-88.

Ohuchi et al., "Oligosaccharides in the Stem Region Maintain the Influenza Virus Hemagglutinin in the Metastable Form Required for Fusion Activity," J. Virol., May 1997, 71 (5):3719-3725.

Pica et al., "$\Delta^{12}$-Prostaglandin $J_2$ is a Potent Inhibitor of Influenza A Virus Replication," Antimicrobial Agents and Chemotherapy, Jan. 2000, 44(1):200-204.

Roberson et al., "Influenza Induces Endoplasmic Reticulum Stress, Caspase-12-Dependent Apoptosis, and c-Jun N-Terminal Kinase-Mediated Transforming Growth Factor-$\beta$ Release in Lung Epithelial Cells," Am. J. Respir. Cell. Mol. Biol., May 2012, 46(5):573-581.

Rossi et al., "Anti-inflammatory cyclopentenone prostaglandins are direct inhibitors of I$\kappa$B kinase," Nature, Jan. 6, 2000, 403:103-108.

Rossignol et al., "Thiazolides, a New Class of Anti-influenza Molecules Targeting Viral Hemagglutinin at the Post-translational Level," Journal of Biological Chemistry, Oct. 23, 2009, 284(43):29798-29808.

Sarge et al., "Activation of Heat Shock Gene Transcription by Heat Shock Factor 1 Involves Oligomerization, Acquisition of DNA-Binding Activity, and Nuclear Localization and Can Occur in the Absence of Stress," Mol. Cell. Biol., Mar. 1993, 13(3):1392-1407.

Soldà et al., "Consequences of ERp57 Deletion on Oxidative Folding of Obligate and Facultative Clients of the Calnexin Cycle," J. Biol. Chem., Mar. 10, 2006, 281(10):6219-6226.

Tatu et al., "Folding and oligomerization of influenza hemagglutinin in the ER and the intermediate compartment," EMBO J., 1995, 14(7):1340-1348.

INHIBITION OF PROTEIN DISULFIDE-ISOMERASE A3

PRIORITY

The present application is the U.S. National Stage of PCT/US2018/027900, filed Apr. 17, 2018, which claims priority to U.S. provisional application no. 62/486,616 filed Apr. 18, 2017, which is incorporated herein by reference in its entirety.

SEQUENCE LISTING

The instant application contains a Sequence Listing which has been submitted in ASCII format via EFS-WEB and is hereby incorporated by reference in its entirety. Said ASCII copy, created on Oct. 7, 2019, is named sequence.txt and is 526 bytes.

FIELD

The present application relates to inhibiting a protein disulfide-isomerase A3 (PDIA3), and for treating diseases and conditions by inhibiting activity of PDIA3, as well as screening for therapeutic agents based on PDIA3 inhibition.

SUMMARY

One embodiment is a method of treating a disease or condition associated with an increased level of expression of protein disulfide-isomerase A3 comprising administering to a subject in need thereof a protein disulfide-isomerase A3-inhibiting effective amount of a pharmaceutical composition comprising at least one thiazolide compound.

FIGURES

FIG. 1 shows that influenza A virus hemagglutinin (HA) interacts with disulfide isomerase PDIA3 in nitazoxanide (NTZ)-treated MDCK cells. HA-PDIA3 interactions (visualized as red spots) detected at 10 h p.i. by PLA in MDCK cells mock-infected (Control) or infected with influenza A virus H1N1 A/Puerto Rico/8/34 (PR8) (3 PFU/cell) and treated with 10 µg/ml NTZ or vehicle after virus adsorption. Nuclei are stained with DAPI (blue). Images were captured with Olympus Fluoview FV-1000 confocal laser scanning system. MERGE and Zoom images are shown.

Figure 2:
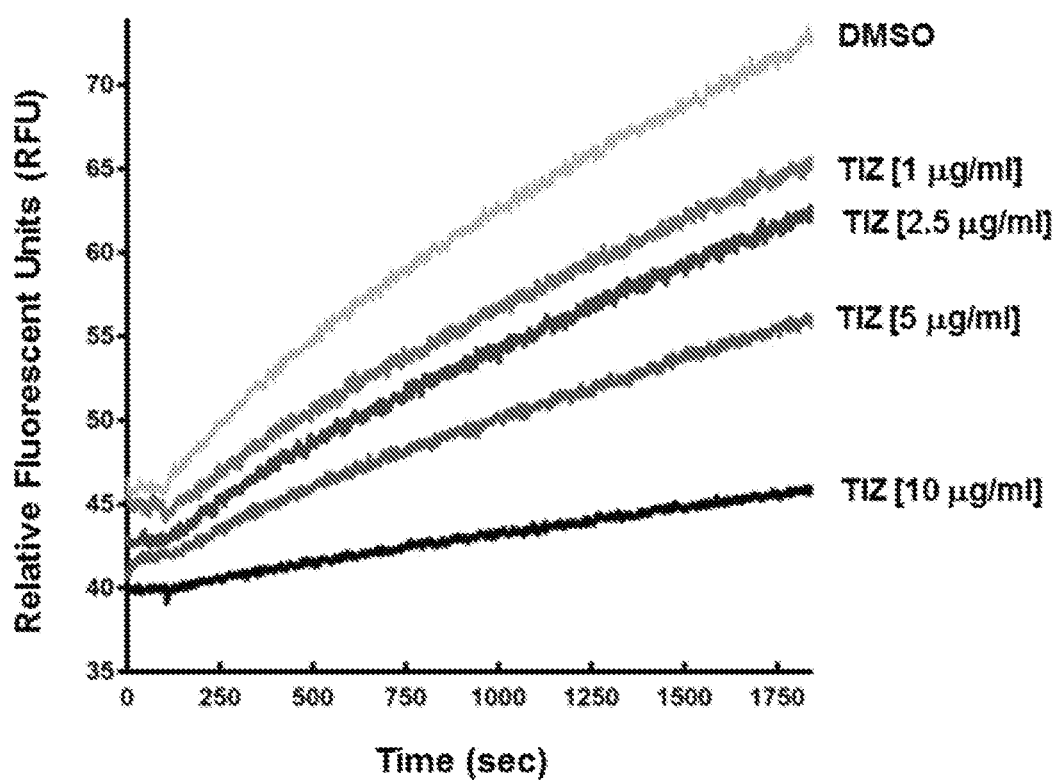

FIG. 2 shows that tizoxanide (TIZ) inhibits disulfide isomerase PDIA3 activity. PDIA3 activity was determined by enzyme-dependent disulfide reduction assay. The disulfide reductase activity was tested in vitro using dieosin glutathione disulfide (Di-E-GSSG) as substrate. Recombinant human PDIA3 (rhPDIA3) (2 nM), pre-incubated with different concentrations of TIZ or control diluent (DMSO) for 10 min. at room temperature, was added to Di-E-GSSG (150 nM) in the presence of 5 µM DTT (arrow). PDIA3 reductase activity cleaves the S—S bond of Di-E-GSSG resulting in the release of fluorescent 2-eosin-GSH (EGSH). The increase in fluorescence was monitored at $\lambda=545$ nm with excitation at $\lambda=525$ nm, and expressed as relative fluorescence units (RFU).

FIG. 3A-B provide kinetic analysis of disulfide isomerase activity for TIZ as an PDIA3 inhibitor. The rhPDIA3 (20 nM), pretreated with TIZ (50 µg/ml) or control diluent (DMSO) for 10 min. at room temperature, was incubated with different concentrations of Di-E-GSSG as described in Materials and Methods. Initial rates ($V_0$) of EGSH formation were monitored as a function of Di-E-GSSG concentration. Theoretical hyperbolic curves as predicted by the Michaelis-Menten equation were plotted (A). Lineweaver-Burk plots represent the inverse of the Michaelis-Menten curves for TIZ (50 µg/ml) vs DMSO (B).

FIG. 4A-B show effect of TIZ on PDIA3 and PDIA1 disulfide reductase activity. Effect of TIZ (5 µg/ml) on PDIA3 and PDIA1 (PDI) activities were measured by Di-E-GSSG assay using the same concentration (20 nM) of PDIA3 or PDIA1.

FIG. 5A-C show that PDIA3 silencing inhibits WSN IAV replication in A549 cells. A549 cells were transiently transfected with PDIA3 (siPDIA3) or control (scrambled, scr) siRNAs and, after 48 h, were infected with 1 PFU/cell (A) or 3 PFU/cell (B) WSN influenza A virus. Virus yield, determined at 16 h p.i. by HA titration in the supernatant of infected cells, represents the mean±SD of duplicate samples. *: $p<0.01$. In parallel, whole-cell extracts from the same samples were analyzed for levels of PDIA3 protein by Western blot analysis (C). Levels of β-actin are shown as control. Scr: scramble control; siPDIA3: PDIA3-silenced samples (48 h).

FIG. 6A-D show that PDIA3 silencing inhibits WSN IAV replication and HA transport to the plasma membrane in A549 cells. A549 cells were transiently transfected with PDIA3 (siPDIA3) or scrambled (control) siRNAs and, after 48 h, were infected with WSN virus (3 PFU/cell) or mock-infected (Mock). At 6 h p.i. erythrocytes adsorbed on plasma-membrane (indicated by red arrows) were detected by phase contrast microscopy (A); hemoglobin levels of bound erythrocytes were quantified spectrophotometrically $\lambda=540$ nm) (B). Data, expressed in optical density (O.D.), represent the means±S.D. of duplicate samples from a representative experiment of two with similar results. *=$p<0.05$ vs infected-control. (C) Immunoblot analysis of HA, PDIA3 and α-tubulin levels in mock-infected (Mock) and WSN-infected (WSN) (6 h p.i.) A549 cells transfected with PDIA3 (+siPDIA3) or control (−siPDIA3) siRNAs. (D) Virus yield, determined at 24 h p.i. by HA titration in the supernatant of infected cells, represents the mean±SD of duplicate samples. *=$p<0.01$.

Figure 7:
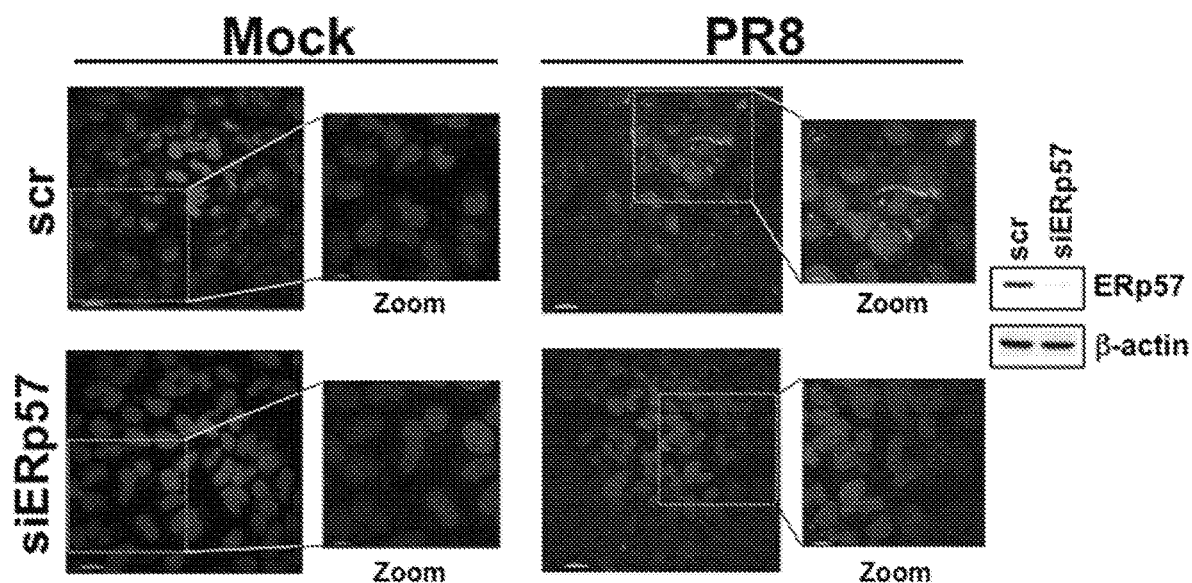

FIG. 7 shows that PDIA3 silencing inhibits PR8 IAV HA transport to the plasma membrane in A549 cells. A549 cells were transiently transfected with PDIA3 (si-PDIA3) or control (scr) siRNAs and, after 48 h, cells were infected with PR8 virus (5 PFU/cell) or mock infected (Mock). Levels of plasma-membrane HA (green) were detected at 6 h p.i. by indirect immunofluorescence in non-permeabilized mock-infected and PR8-infected cells. Nuclei are stained with Hoechst-33342 (blue). Images were captured with Olympus Fluoview FV-1000 confocal laser scanning system. Overlay of the two fluorochromes is shown. Enlarged areas (Zoom) highlight HA membrane localization. PDIA3 and α-tubulin levels detected by Western blot before PR8 infection in siPDIA3-silenced and control cells are shown on the left. PDIA3-silencing markedly decreases HA plasma membrane levels.

Figure 8:
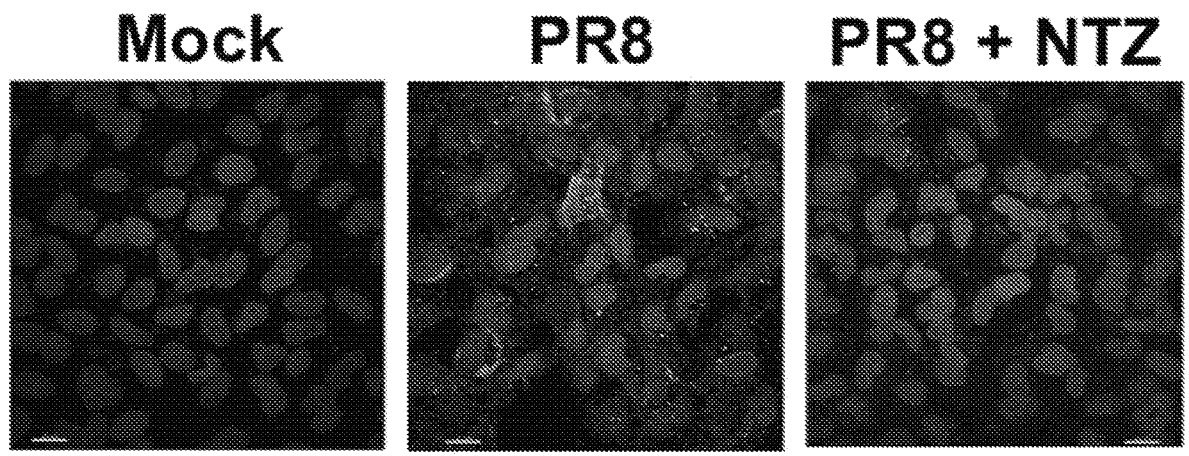

FIG. 8 shows NTZ inhibits PR8 IAV HA transport to the plasma membrane in A549 cells. A549 cells were infected with PR8 IAV (5 PFU/cell) (PR8) or mock-infected (Mock), and treated with NTZ (5 µg/ml) or vehicle immediately after the virus adsorption period. At 6 h p.i., the presence of plasma membrane-incorporated HA (green) was determined by indirect immunofluorescence in non-permeabilized cells. Nuclei are stained with Hoechst-33342 (blue). Merge images are shown.

DETAILED DESCRIPTION

Unless otherwise specified, "a" or "an" means "one or more."

Protein disulfide-isomerase A3 (PDIA3), also known as glucose-regulated protein, 58-kD (GRP58), is an isomerase enzyme. Other names for PDIA3 include ER60, ERp57, ERp60, ERp61, GRP57, GRP58, HEL-S-269, HEL-S-93n, HsT17083, P58, and PI-PLC.

The present inventors discovered that thiazolide compounds, such as nitazoxanide or tizoxanide, are surprisingly effective at inhibiting protein disulfide-isomerase A3 (PDIA3). Accordingly, the thiazolide compounds may be used for treating a disease or condition, which is associated with PDIA3 expression, and/or for treating a disease or condition for which PDIA3 inhibition is a mechanism of treatment. Further, an increased level of PDIA3 expression in a subject may identify that a subject is suffering from such a disease or condition.

One embodiment is a method of treating a subject in need of inhibition of PDIA3 with a thiazolide compound, preferably NTZ or TIZ. Preferably, the thiazolide compound has an IC50 inhibitory value against PDIA3 of less or no more than 10 µg/ml or less or no more than 9 µg/ml or less or no more than 8 µg/ml or less or no more than 7 µg/ml or less or no more than 6 µg/ml or less or no more than 5 µg/ml or less or no more than 4 µg/ml or less or no more than 3 µg/ml or less or no more than 2 µg/ml. Even more preferably, the thiazolide compound selectively inhibits PDIA3 but has less inhibitory activity towards one or more other PDIs, such as PDIA1. In other words, the thiazolide compound may have a lower IC50 inhibitory value for PDIA3 inhibition than an IC50 inhibitory value for one or more other PDIs, such as PDIA1. For example, the thiazolide compound may have an IC50 inhibitory value for PDIA3 inhibition that is at least 1.5 times or at least 2 times or at least 3 times or at least 5 times or at least 10 times or at least 15 times or at least 20 times or at least 50 times or at least 100 times lower than an IC50 inhibitory value for one or more other PDIs, such as PDIA1. In some embodiments, In the thiazolide compound may have a lower IC50 inhibitory value for PDIA3 inhibition than an IC50 inhibitory value for any other PDIs. For example, the thiazolide compound may have an IC50 inhibitory value for PDIA3 inhibition that is at least 1.5 times or at least 2 times or at least 3 times or at least 5 times or at least 10 times or at least 15 times or at least 20 times or at least 50 times or at least 100 times lower than an IC50 inhibitory value for any other PDIs.

Another embodiment is a method of identifying a therapeutic agent for use in treating a cancer or a non-cancer disease condition, such as a viral infection, by measuring its inhibitory activity against PDIA3, wherein a higher level of inhibition correlates with its efficacy in treating a cancer or a viral infection. Preferably, a candidate agent is determined to be a therapeutic agent if it has an IC50 inhibitory value against PDIA3 of less or no more than 10 µg/ml or less or no more than 9 µg/ml or less or no more than 8 µg/ml or less or no more than 7 µg/ml or less or no more than 6 µg/ml or less or no more than 5 µg/ml or less or no more than 4 µg/ml or less or no more than 3 µg/ml or less or no more than 2 µg/ml. Even more preferably, the candidate agent should selectively inhibit PDIA3 but have less inhibitory activity towards other PDIs. In other words, the candidate agent may have a lower IC50 inhibitory value for PDIA3 inhibition than an IC50 inhibitory value for one or more other PDIs, such as PDIA1. For example, the candidate agent may have an IC50 inhibitory value for PDIA3 inhibition that is at least 1.5 times or at least 2 times or at least 3 times or at least 5 times or at least 10 times or at least 15 times or at least 20 times or at least 50 times or at least 100 times lower than an IC50 inhibitory value for one or more other PDIs, such as PDIA1. In some embodiments, In the candidate agent may have a lower IC50 inhibitory value for PDIA3 inhibition than an IC50 inhibitory value for any other PDIs. For example, the candidate agent may have an IC50 inhibitory value for PDIA3 inhibition that is at least 1.5 times or at least 2 times or at least 3 times or at least 5 times or at least 10 times or at least 15 times or at least 20 times or at least 50 times or at least 100 times lower than an IC50 inhibitory value for any other PDIs.

As indicated above, a subject in need of treatment suffering from a cancer can be treated by administering an effective amount of a PDIA3 inhibitor. Examples of such cancers include liver cancer, such as hepatocellular carcinoma; breast cancer, including those with ductal carcinomas and those with bone metastasis; colon cancers; colorectal cancers; melanoma; carcinoid; glioma; head and neck cancer, such as oral squamous cell carcinoma; lymphoma; urothelial cancer; uterus cancer; lung cancer; ovarian cancer, such as epithelial ovarian cancer; stomach cancer; cervical cancer; gallbladder cancer; squamous cancers; adenocarcinomas; bronchioalveolar carcinomas; astrocytomas; glioblastomas; kidney carcinoma. In some embodiments, the cancer may be a cancer involving bone metastasis.

In some embodiments, administering of a thiazolide compound, such as nitazoxanide and/or tizoxanide, to a subject, which can be, for example, such as a human being, may result in reduction of proliferation of cancer and/or tumor cells in the subject. In some embodiments, administering of a thiazolide compound, such as nitazoxanide and/or tizoxanide, to a subject, which can be, for example, such as a human being, may result in increased apoptosis of cancer and/or tumor cells in the subject. Yet in some embodiments, administering of a thiazolide compound, such as nitazoxanide and/or tizoxanide, to a subject, which can be, for example, such as a human being, may result in reduction of proliferation of cancer and/or tumor cells and in increased apoptosis of cancer and/or tumor cells in the subject.

In some embodiments, a disease or condition which can be treated by PDIA3 inhibition may be a non-cancerous disease or condition. Examples of such disease or condition may be a viral infection, renal fibrosis, liver fibrosis, or a neurodegenerative disease, such as Creutzfekdt-Jacob disease, Huntington's disease or Alzheimer's disease.

A thiazolide compound, such as nitazoxanide and/or tizoxanide, may be preferably administered to a subject, which may be a mammal, such as a human being, in an amount, which is effective to inhibit protein disulfide-isomerase A3.

In some embodiments, the thiazolide compound may be nitazoxanide (NTZ, 1, see formula below) or a pharmaceutically acceptable salt thereof. Nitazoxanide is a licensed product in the United States for the treatment of infectious gastroenteritis. In some embodiments, the thiazolide compound may be tizoxanide (TIZ, 2, see formula below) or its pharmaceutically acceptable salt.

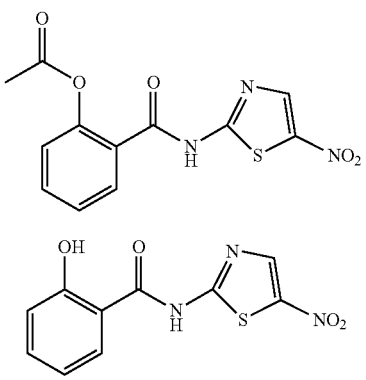

(NTZ, 1)

(TIZ, 2)

In some embodiments, nitazoxanide and tizoxanide may be used together as a combination. Thiazolide compounds may be synthesized, for example, according to published procedures U.S. Pat. Nos. 3,950,351 and 6,020,353, PCT WO2006042195A1 and US2009/0036467A. Thiazolide compounds are disclosed in U.S. Pat. Nos. 7,645,783, 7,550,493, 7,285,567, 6,117,894, 6,020,353, 5,968,961, 5,965,590, 5,935,591, 5,886,013.

The term "salt" may be used in its broadest sense. For example, the term "salt" includes hydrogen salts and hydroxide salts with ions of the present compound. In some embodiments, the term salt may be a subclass referred to as pharmaceutically acceptable salts, which are salts of the present compounds having a pharmacological activity and which are neither biologically nor otherwise undesirable. In all embodiments, the salts can be formed with acids, such as, without limitation, hydrogen, halides, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycero-phosphate, hemisulfate, heptanoate, hexanoate, hydrochloride hydrobromide, hydroiodide, 2-hydroxyethane sulfonate, lactate, maleate, methanesulfonate, 2-naphthalenesulfonate, nicotinate, oxalate, thiocyanate, tosylate, and undecanoate. In all embodiments, the salts can be formed with bases, such as, without limitation, hydroxide, ammonium salts, alkali metal salts such as lithium, sodium and potassium salts, alkaline earth metal salts such as calcium, magnesium salts, aluminum salts, salts with organic bases such as ammonia, methylamine, diethylamine, ethanolamine, dicyclohexylamine, N-methylmorpholine, N-methyl-D-glucamine, and salts with amino acids such as arginine and lysine. Basic nitrogen-containing groups can be quaternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides. The terms "therapeutically acceptable salt," and "pharmaceutically acceptable salt," as used herein, represent both salts and zwitterionic forms of the compounds of the present invention which are water or oil-soluble or dispersible; which are suitable for treatment of diseases without undue toxicity, irritation, and allergic response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzene sulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethane sulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reacting a carboxyl, phenol or similar group with a suitable base such as a metal hydroxide, carbonate, or bicarbonate, or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

In some embodiments, the thiazolide compound may be administered as a part of a pharmaceutical composition. The pharmaceutical composition may include in addition to the thiazolide compound may include a carrier, such as a pharmaceutically acceptable carrier. The term "carrier" may be used in its broadest sense. For example, the term "carrier" refers to any carriers, diluents, excipients, wetting agents, buffering agents, suspending agents, lubricating agents, adjuvants, vehicles, delivery systems, emulsifiers, disintegrants, absorbents, preservatives, surfactants, colorants, flavorants, and sweeteners. In some embodiments, the carrier may be a pharmaceutically acceptable carrier, a term narrower than carrier, because the term pharmaceutically acceptable carrier" means a non-toxic that would be suitable for use in a pharmaceutical composition. Actual dosage levels of active ingredients in the pharmaceutical compositions may vary so as to administer an amount of the active compound(s) that is effective to achieve the desired therapeutic response for a particular patient.

The selected dose level may depend on the activity of the thiazolide compound, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient may depend on a variety of factors, including the body weight, general health, diet, time and route of administration and combination with other therapeutic agents and the severity of the condition or disease being treated.

The pharmaceutical compositions may be administered systemically, for example, in an oral formulation, such as a solid oral formulation. For example, it may be in the physical form of a powder, tablet, capsule, lozenge, gel, solution, suspension, syrup, or the like. In some embodiments, the pharmaceutical composition may be in a form of a formulation disclosed in U.S. Pat. No. 8,524,278. Such formulation may, for example, include a controlled release portion, which includes a thiazolide compound, such as nitazoxanide and/or tizoxanide; and an immediate release portion, which contains a thiazolide compound, such as nitazoxanide and/or tizoxanide. These compositions may be administered in a single dose or in multiple doses which are administered at different times.

In some embodiments, the total amount of a thiazolide compound, such as nitazoxanide and/or tizoxanide, in the composition may be about 60% to 75% by weight of the composition. The composition may be formulated for immediate release, controlled release or sustained release. The compositions may contain one or more additional pharmaceutically acceptable additives or excipients. These excipients are therapeutically inert ingredients that are well known and appreciated in the art. As used herein, the term "inert ingredient" may refer to those therapeutically inert ingredients that are well known in the art of pharmaceutical science, which can be used singly or in various combinations, and include, for example, diluents, disintegrants, binders, suspending agents, glidants, lubricants, fillers, coating agents, solubilizing agent, sweetening agents, coloring agents, flavoring agents, and antioxidants. See, for example, Remington: The Science and Practice of Pharmacy 1995, edited by E. W. Martin, Mack Publishing Company, 19th edition, Easton, Pa.

Examples of diluents or fillers include, but are not limited to, starch, lactose, xylitol, sorbitol, confectioner's sugar, compressible sugar, dextrates, dextrin, dextrose, fructose, lactitol, mannitol, sucrose, talc, microcrystalline cellulose, calcium carbonate, calcium phosphate dibasic or tribasic, dicalcium phosphate dehydrate, calcium sulfate, and the like. The amount of diluents or fillers may be in a range between about 2% to about 15% by weight of the entire composition. Examples of disintegrants include, but are not limited to, alginic acid, methacrylic acid DVB, cross-linked PVP, microcrystalline cellulose, sodium croscarmellose, crospovidone, polacrilin potassium, sodium starch glycolate, starch, including corn or maize starch, pregelatinized starch and the like. Disintegrant(s) typically represent about 2% to about 15% by weight of the entire composition.

Examples of binders include, but are not limited to, starches such as potato starch, wheat starch, corn starch; microcrystalline cellulose; celluloses such as hydroxypropyl cellulose, hydroxyethyl cellulose, hydroxypropylmethyl cellulose (HPMC), ethyl cellulose, sodium carboxy methyl cellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, and the like. The amount of binders is about 0.2% to about 14% by weight of the entire composition.

Examples of glidants include, but are not limited to, silicon dioxide, colloidal anhydrous silica, magnesium trisilicate, tribasic calcium phosphate, calcium silicate, magnesium silicate, colloidal silicon dioxide, powdered cellulose, starch, talc, and the like. The amount of glidant(s) is about 0.01% to about 0.3% by weight of the entire composition.

Examples of lubricants include, but are not limited to, magnesium stearate, aluminum stearate, calcium stearate, zinc stearate, stearic acid, polyethylene glycol, glyceryl behenate, mineral oil, sodium stearyl fumarate, talc, hydrogenated vegetable oil and the like. The amount of lubricant (s) is about 0.2% to about 1.0% by weight of the entire composition.

The compositions may contain a binder that is a low-viscosity polymer. Examples of low-viscosity polymers include, but are not limited to, low-viscosity hydroxypropyl methylcellulose polymers such as those sold by Dow Chemical under the tradename "MethoceL™" (e.g., Methocel E50LV™, Methocel K100LVR™, and Methocel F50LVR™) and low-viscosity hydroxyethylcellulose polymers. The low-viscosity polymer is typically present at about 10% to about 20%, or about 10% to about 15%, or preferably about 12%, of the total weight of the entire composition, or, in those embodiments having controlled release and immediate release portions, the low-viscosity polymer in the controlled release portion is typically present at about 15% to about 20%, preferably about 18%, of the weight of the controlled release portion.

The compositions may further comprise a coating material. The coating material is typically present as an outer layer on the dosage form that completely covers the formulation. For example, in some embodiments, the dosage form is an oral tablet in which the controlled release portion forms a first layer of the tablet and the immediate release portion forms a second layer that is deposited on top of the first layer to form a core tablet. In such embodiments, e.g., the coating material can be in the form of an outer coating layer that is deposited on top of the core tablet. The coating material typically is about 1% to about 5% by weight of the composition, and may comprise hydroxypropylmethylcellulose and/or polyethylene glycol, and one or more excipients selected from the group comprising coating agents, opacifiers, taste-masking agents, fillers, polishing agents, coloring agents, antitacking agents and the like. Examples of film-coating substances and methods for using such coating substances are well known to those of skill in the art.

In some embodiments, a daily dose of a thiazolide compound, such as nitazoxanide and/or tizoxanide, administered to a human may be from 100 mg to 1300 mg or from 200 mg to 1200 mg or from 250 mg to 1100 mg or from 300 mg to 1000 mg or any dose value or subrange within these ranges. Exemplary dosage values include 100 mg, 200 mg, 300 mg, 400 mg, 500 mg, 600 mg, 700 mg or 800 mg.

Embodiments described herein are further illustrated by, though in no way limited to, the following working examples.

EXAMPLES

The present study investigates the mechanism by which NTZ and TIZ inhibit maturation and intracellular transport of the influenza virus hemagglutinin.

MATERIALS AND METHODS

Cell Culture, Treatment and Transfections. Human A549 alveolar type II-like epithelial cells and canine Madin-Darby kidney (MDCK) cells were grown at 37° C. in a 5% $CO_2$ atmosphere in RPMI medium (Gibco-Invitrogen, Carlsbad, Calif.) supplemented with 10% fetal calf serum (FCS), 2 mM glutamine and antibiotics.

NTZ, TIZ (Romark Laboratories, L.C.) dissolved in DMSO stock solution (25 mg/ml) were diluted in culture medium and added to infected cells immediately after a one-hour adsorption period, unless differently specified. Compounds were maintained in the medium for the duration of the experiment. Controls received equal amounts of DMSO vehicle, which did not affect cell viability or virus replication. Each concentration of each compound was tested in duplicate and each experiment was repeated at least twice.

Cytotoxicity.

Cell viability was determined by the 3-(4,5-dimethylthi-azol-2-yl)-2,5-diphenyltetrazolium bromide (MTT) to MTT formazan conversion assay (Sigma-Aldrich, St Louis, Mo.). For MTT assay, reduced MTT (formazan) was extracted from cells by adding 100 µl of acidic isopropanol containing 10% Triton X-100, and formazan absorbance was measured in an ELISA microplate reader at two different wavelengths (540 and 690 nm). The 50% lethal dose ($LD_{50}$) was calculated using Prism 5.0 software (Graph-Pad Software Inc., San Diego, Calif.). Microscopical examination of mock-infected or virus-infected cells was performed daily to detect the cytopathic effect induced by the different viruses, and possible morphological changes and/or cytoprotection induced by the drug. Microscopy studies were performed using a Leica DM-IL microscope and images were captured on a Leica DC 300 camera using Leica Image-Manager 500 software.

Virus Preparation, Infection and Titration.

Influenza A virus (IAV) H1N1 A/Puerto Rico/8/34 (PR8) and A/WSN/33 (WSN) were grown in the allantoic cavity of 8-day-old embryonated eggs. After 48 h at 37° C., the allantoic fluid was harvested and centrifuged at 5,000 rpm for 30 minutes to remove cellular debris, and virus titers were determined by hemagglutinin titration and plaque assay, according to standard procedures (Bernasconi et al., 2005, Pica et al., 2000).

For viral infection, confluent MDCK cell monolayers were infected with IAV for 1 hour at 37° C. at a multiplicity of infection (MOI) of 3 PFU (Plaque Forming Unit)/cell, unless differently specified. Similar conditions were utilized for infection of human A549 cells. After the adsorption period, the viral inoculum was removed, and cell monolayers were washed three times with phosphate-buffered saline (PBS). The cells were maintained at 37° C. in RPMI 1640 culture medium containing 2% fetal calf serum. For multi-step virus growth curves, confluent MDCK/A549 cell monolayers were infected with influenza viruses for 1 h at 37° C. at an MOI of 0.01 PFU/cell. After the 1 h adsorption period, the viral inoculum was removed, and cell monolayers were washed three times with PBS. Cells were maintained at 37° C. in RPMI 1640 culture medium containing 0.5% bovine serum albumin (BSA) and L-1-tosylamide-2-phenylethyl chloromethyl ketone (TPCK)-treated trypsin (1 µg/ml) (Sigma-Aldrich). Virus yield was determined 24 and 48 h post infection (p.i.) by HA titration or by plaque assay, as previously described (Belardo et al., 2015). For the plaque assay, serial 10-fold dilutions of the different viruses were prepared and inoculated on confluent MDCK cell monolayers in 35-mm plates (Corning, New York, N.Y.). After 1 h at 37° C., the inoculum was removed and the cells were washed three times with PBS before the addition of RPMI containing 0.5% BSA, 1 µg/ml TPCK-treated trypsin, and 0.5% SeaPlaque agarose (Lonza). After 72 h at 37° C., the overlay was removed and cells were fixed with 4% paraformaldehyde in phosphate-buffered saline (Sigma-Aldrich) and stained with 1% crystal violet (Sigma-Aldrich). The $IC_{50}$ (50% inhibitory concentration) and $IC_{90}$ (90% inhibitory concentration) of the different antiviral compounds was calculated using Prism 5.0 software.

For Western blot analysis, cell extracts (25 µg) were separated by SDS-PAGE and blotted to nitrocellulose, and filters were incubated with the following antibodies: polyclonal anti-α-tubulin (11H10; Cell Signaling Technology Inc.), anti-β-actin (Sigma-Aldrich), anti-influenza A/PR/8/34 antibodies (a kind gift of Dr. E. Rodriguez Boulan, Cornell University, NY), anti-hemagglutinin anti-H2 (eEnzyme LLC, Gaithersburg, Md.), anti-H5 (P20; Santa Cruz Biotechnology Inc., Santa Cruz, Calif.) and anti-H7 (GeneTex Inc., Irvine, Calif.) antibodies or monoclonal anti-H1 (IVC102; Biodesign Inc., Saco, Me. C102; Santa Cruz Biotechnology Inc.), anti-PDIA3 (MaP.PDIA3; Santa Cruz Biotechnology) and anti-α-tubulin (B-5-1-2, Sigma-Aldrich) antibodies, followed by decoration with peroxidase-labeled anti-rabbit IgG, anti-goat IgG or anti-mouse IgG (SuperSignal detection kit; Pierce).

siRNA Interference.

siRNA duplex sequences, si-PDIA3 (5'-TCCAGC-CAACAAGAAGCTAAA-3'), (SEQ ID NO: 1)), and the scrambled control (scRNA) sequence were purchased from QIAGEN (Hilden, Germany). siRNA (si-PDIA3) were used for PDIA3 silencing. Transfections were performed using jetPRIME Transfection Reagent, (Polyplus-transfection) according to the manufacturer's instructions. Briefly, for PDIA3 silencing, cells were plated on 35-mm wells (1.5× $10^5$ cells/well) and, after 18 h, were transfected with 60 nM of the indicated siRNA or scrambled control. After 24 h cells were washed twice with culture medium and transfections were repeated as above. For WSN IAV infection experiments, at 48 h after transfection siRNAs and scRNA were removed, and cells were washed twice with culture medium and subjected to WSN or PR8 IAV infection (1, 3 or 5 PFU/cell) as described above. After the adsorption period, the viral inoculum was removed, and cell monolayers were washed three times with PBS.

Hemadsorption Assay.

A546 cell monolayers were transfected with si-PDIA3 or scRNA control as described above. After 48 h, cells were infected with WSN (5 PFU/cell) or mock-infected. At 6 h p.i., the cells were washed three times with PBS and incubated with 0.1% of human red blood cells in PBS for 20 minutes at 4° C. to inhibit neuraminidase activity. After removal of unbound erythrocytes by washing three times with PBS, red blood cells adsorbed on A549 cell surface were detected by phase contrast microscopy. The images were captured with a Leica DMLB microscope equipped with a Leica DC300 camera, using Leica Image-Manager500 software. Adherent erythrocytes were lysed in 150 mM $NH_4Cl$ buffer for 2 h at room temperature and quantified by measuring hemoglobin absorbance at λ=540 nm (Glaser et al., 2007).

Immunofluorescence Microscopy.

PR8-infected MDCK and A549 cells grown on coverslips were fixed with 4% paraformaldehyde in phosphate-buffered saline for 20 minutes at room temperature at 16 or 24 h p.i., respectively. Mock-infected cells were processed similarly. Fixed cells were either incubated with anti-HA antibodies for 1 h at 37° C. for plasma membrane staining, or were permeabilized with 0.1% TritonX-100-PBS for 10 minutes at room temperature and then incubated with monoclonal anti-HA or polyclonal anti-α-tubulin (11H10; Cell Signaling, Technology Inc.) antibodies for 1 h at 37° C., followed by decoration with Alexa Fluor488-conjugated (Molecular Probes-Invitrogen) or rhodamine-conjugated (Pierce) goat anti-mouse IgG, and rhodamine-conjugated goat anti-rabbit IgG (Pierce). The nuclei were stained with 4',6-diamidino-2-phenylindole (DAPI) or Hoechst 33342 (Molecular Probes, Invitrogen). Images were captured using an Olympus Fluoview FV1000 confocal laser scanning system (Olympus America Inc., Center Valley, Pa.) based on Olympus Ix81 inverted microscope equipped with Olympus Plan-Apochromat 60× oil-immersion objective. Images (800×800 pixels resolution) were analyzed using Imaris 6.2 software (Bitplane, Zurich, CH). Images shown in all figures are representative of at least five random fields (scale-bars are indicated). Control incubations demonstrated non-cross-reactivity between the anti-immunoglobulin conjugates or between the anti-immunoglobulin conjugate and the irrelevant primary antibody. Images of a representative experiment of three with similar results are shown.

Proximity Ligation Assay (PLA).

For PLA-assay, cells were grown on coverslips and processed as described above. After incubation with the primary antibodies, Duolink in situ PLA (Sigma-Aldrich) was performed according to the manufacturer's protocol. Briefly, PLA probes were incubated for 1 h at 37° C., followed by hybridization, ligation (30 min at 37° C.) and amplification (100 min at 37° C.). Nuclei were stained with DAPI in Duolink In Situ Mounting Medium (Sigma). Antibodies used are: polyclonal anti-PDIA3 (Merck-Millipore); monoclonal anti-HA (sc-52025 Santa Cruz Biotechnology).

Images were captured using an Olympus Fluoview FV1000 confocal laser scanning system (Olympus America Inc., Center Valley, Pa.) based on Olympus Ix81 inverted microscope equipped with Olympus Plan-Apochromat 60× oil-immersion objective. Images (800×800 pixels resolution) were analyzed using Imaris 6.2 software (Bitplane, Zurich, CH). Images shown in all figures are representative of at least five random fields (scale-bars are indicated).

Disulfide Reductase Activity Assay.

Disulfide reductase (DR) activity of PDIA3 or protein disulfide isomerase (PDI) was monitored by sensitive fluorescent assay using dieosin glutathione disulfide (Di-E-GSSG) (Cayman Chemical) as a substrate. DR activity assay was performed in a reaction buffer (0.1 M potassium phosphate, pH 7.0; 2 mM EDTA) by adding 2 or 20 nM of full-length recombinant human PDIA3 (rhPDIA3, Abcam) or PDI (rhPDIA1, R&D Systems) to different concentrations of Di-E-GSSG in the presence of 5 μM DTT. The reductase activity of disulfide isomerases cleaves the S—S bond of Di-E-GSSG resulting in the release of fluorescent 2-eosin-GSH (EGSH). To test the effect of TIZ on PDIA3 and PDI reductase activity, recombinant human PDIA3 or PDIA1 were previously incubated for 10 min at room temperature with different concentrations of TIZ or control diluent (DMSO) in the reaction buffer, unless differently specified. The increase in fluorescence was monitored at λ=545 nm with excitation at λ=525 nm at 25° C. with continuous stirring, and expressed as relative fluorescence units (RFU).

Statistical Analysis. Statistical analysis was performed using Student's t test for unpaired data. The data are expressed as the means±S.D. of duplicate samples. p values of <0.05 were considered significant.

RESULTS

PDIA3-HA protein-protein interaction was then analyzed by proximity ligation assay (PLA) in MDCK cells infected with PR8 virus (3 PFU/cell) and treated with 10 μg/ml NTZ, or vehicle after virus adsorption. As shown in FIG. 1, the PLA colocalization clearly demonstrate that PDIA3 strongly interacts with HA forming large spots in NTZ-treated host cells, but not in control cells. This finding suggests that, in the presence of NTZ, PDIA3 stably binds to the HA-protein in the endoplasmic reticulum. Furthermore, it suggests that perhaps NTZ may affect the PDI PDIA3, inhibiting its co-chaperone disulfide-isomerase activity, thus impairing the correct folding of the HA protein and preventing its trafficking to the host cell plasma-membrane.

Thiazolides inhibit PDIA3 disulfide isomerase activity. To investigate whether thiazolides may directly affect PDIA3 disulfide-isomerase activity, we performed a fluorescence-based reductase in vitro assay using purified full-length recombinant human PDIA3 and oxidized glutathione coupled to dieosin (Di-E-GSSG) as a substrate. NTZ's circulating active metabolite, TIZ, was utilized for these studies.

Recombinant human PDIA3 (rhPDIA3) (2 nM) was pre-incubated with different concentrations of TIZ or control diluent (DMSO) for 10 min. at room temperature. At the end of pre-incubation, Di-E-GSSG (150 nM) was added in the presence of 5 μM DTT to start the enzymatic reaction. PDIA3 reductase activity cleaves the S—S bond of Di-E-GSSG resulting in the release of fluorescent 2-eosin-GSH (EGSH), that is measured in function of time by fluorimetry, as described in Materials and Methods. The results of the time-course shown in FIG. 2 clearly demonstrate that TIZ inhibits PDIA3 activity in a dose-dependent manner. Inhibitory activity was observed at the lowest TIZ concentration tested (1 μg/mL)

Figure 3:
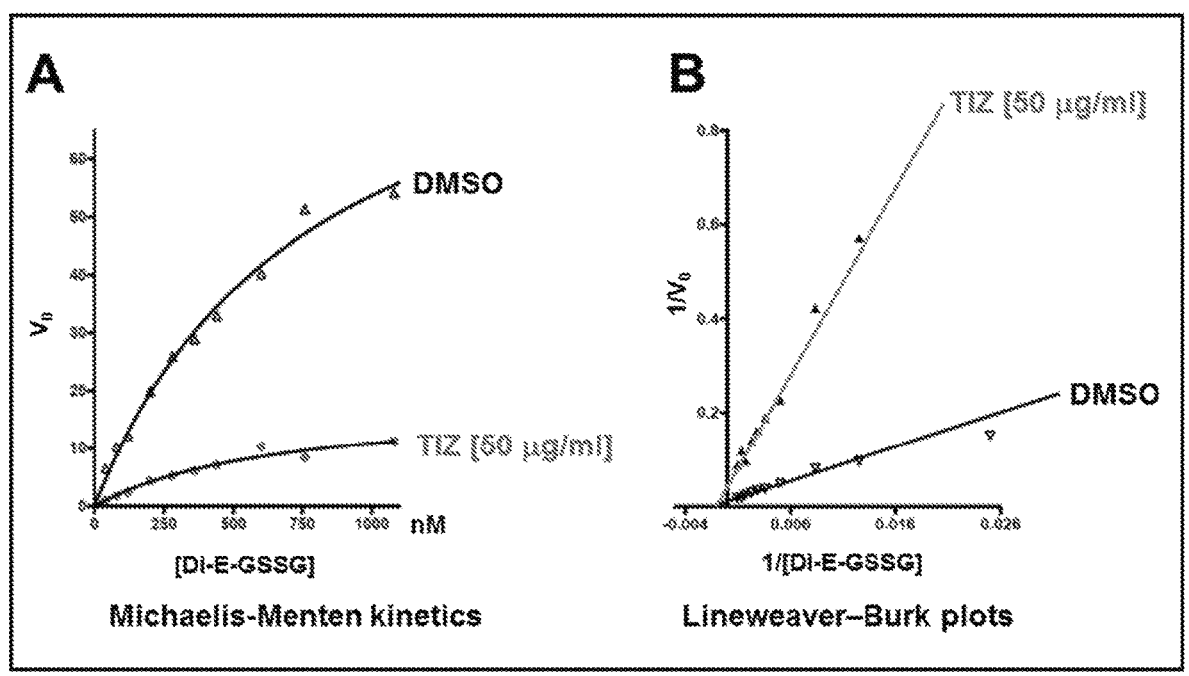

To better understand the effect of TIZ on the PDIA3 activity, a kinetic analysis was performed, where the initial reaction velocity (V0) was determined at varying concentrations of Di-E-GSSG. RhPDIA3 (20 nM) was pre-incubated with 50 μg/ml TIZ or DMSO as described above. The results are shown in FIG. 3 as Michaelis-Menten curves (FIG. 3A) and double-reciprocal (Lineweaver-Burk) plots (FIG. 3B).

Figure 4:
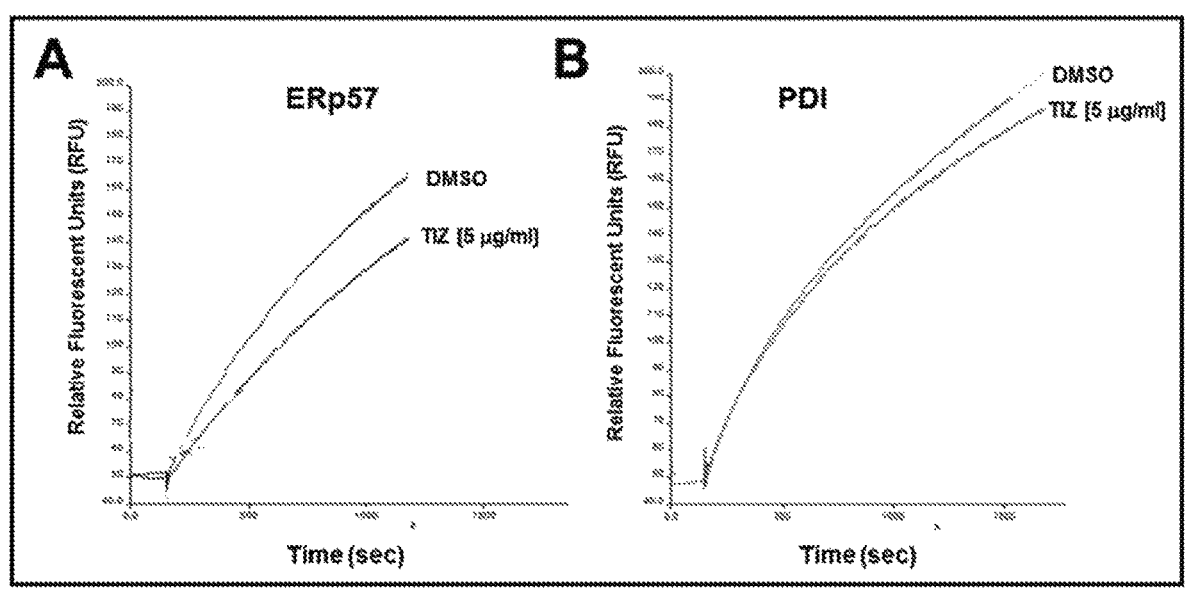

Finally, in a preliminary experiment, we also compared the effect of TIZ on PDIA3 and human PDIA1 reductase activities. The assay was performed as described above using the same concentration of PDIA3 or PDIA1 (20 nM). The results suggest that, at low concentrations, TIZ (5 μg/ml) preferentially inhibits PDIA3 reductase activity in vitro (FIG. 4).

PDIA3 silencing inhibits influenza A virus replication in human lung A549 cells. Previous studies have shown a critical role of PDIA3 in influenza virus HA maturation (Soldà et al., 2006). To investigate the role of PDIA3 on influenza virus replication in our model, human A549 alveolar type II-like epithelial cells ($1.5\times10^5$ cells/well) were transfected twice with PDIA3-siRNA or scrambled control RNA, as described in Materials and Methods. For WSN IAV infection experiments, at 48 h after transfection, siRNAs and scRNA were removed, and cells were washed twice with culture medium and subjected to WSN IAV infection (1 or 3 PFU/cell) as described above. After the adsorption period, the viral inoculum was removed, and cell monolayers were washed three times with PBS. Virus yield was determined at 16 h p.i. by hemagglutinin titration. In parallel samples, levels of PDIA3 and β-actin as control were determined by Western blot analysis.

Figure 5:
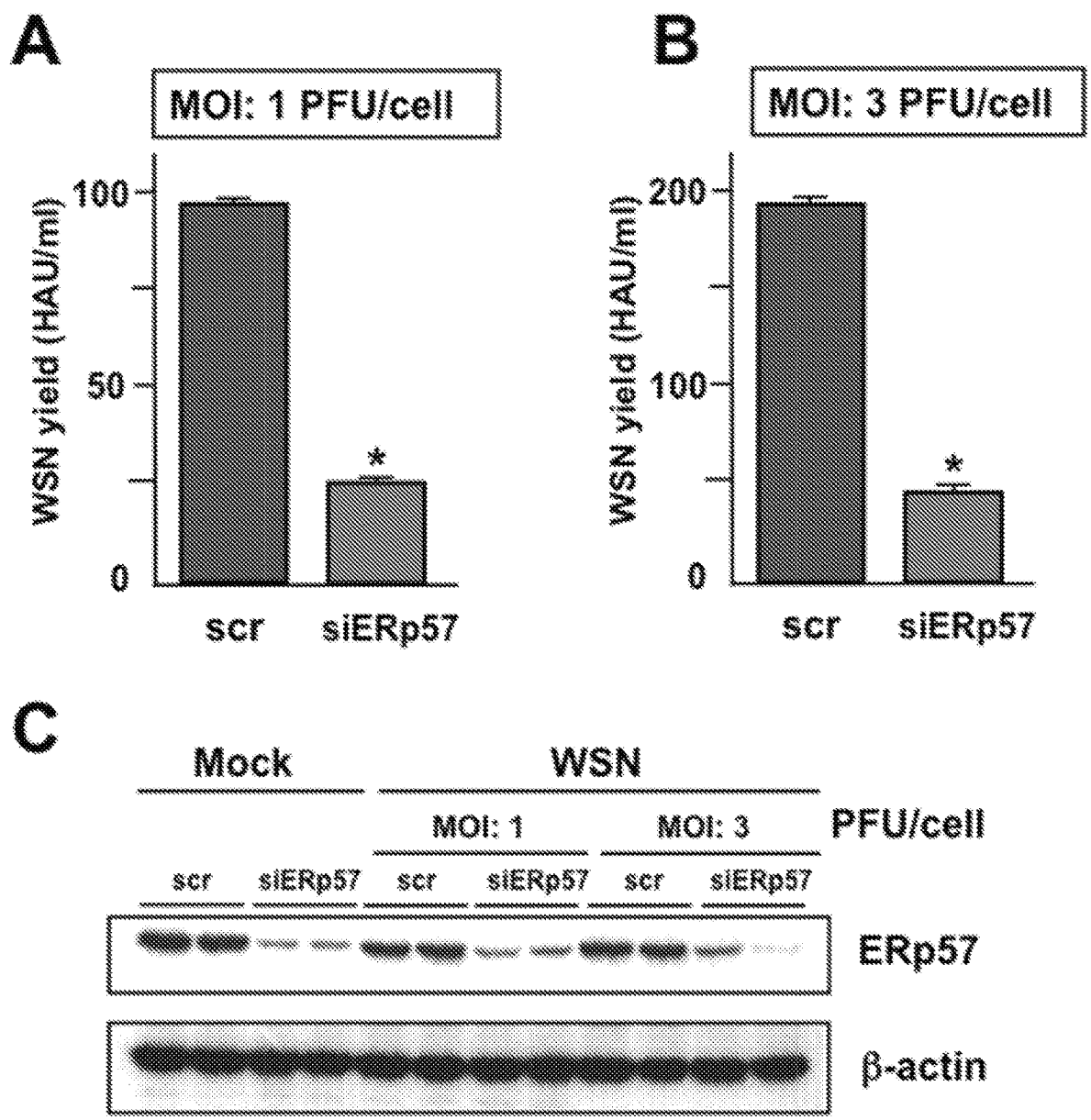

As shown in FIG. 5, levels of PDIA3 were greatly decreased in siPDIA3-silenced cells as compared to scramble-transfected controls. Interestingly, WSN influenza virus replication was greatly impaired by PDIA3 silencing independently of the MOI used.

Figure 6:
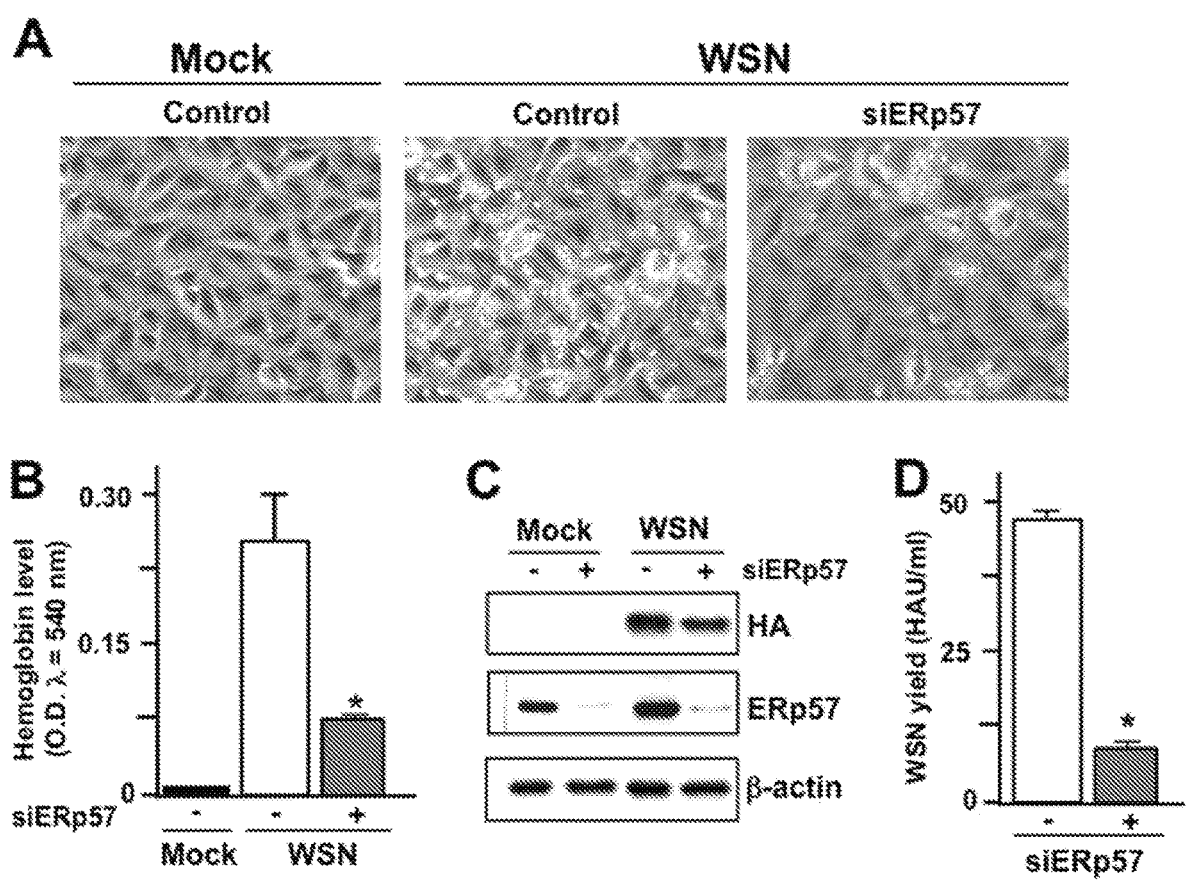

To investigate whether PDIA3 silencing could affect influenza HA maturation and transport to the host cell membrane, A546 cell monolayers were transfected with siPDIA3 or scRNA control as described above. After 48 h, cells were infected with WSN IAV (3 PFU/cell) or mock-infected. At 6 h p.i., the presence of plasma membrane-incorporated HA was determined by receptor-binding (hemadsorption) assay (FIG. 6). After removal of unbound erythrocytes, red blood cells adsorbed on A549 cell surface were detected by phase contrast microscopy (FIG. 6A); hemoglobin levels of bound erythrocytes were also quantified spectrophotometrically (FIG. 6B), as described in Material and Methods. The results clearly show a decrease in bound erythrocytes in PDIA3-silenced cells.

In parallel samples levels of PDIA3 protein and WSN HA were analyzed by Western blot. As shown in FIG. 6C, levels of PDIA3 were greatly decreased in siPDIA3-silenced cells as compared to scramble-transfected controls. Interestingly, PDIA3-silencing caused an alteration in HA electrophoretic mobility comparable to the one previously observed for thiazolides in the WSN influenza virus model (see Rossignol et al., 2009). Virus yield, determined at 24 h p.i. by HA titration in the supernatant of infected cells, was greatly decreased in PDIA3-silenced cells (FIG. 6D). PDIA3 levels were found to be increased in WSN-infected A549 cells (FIG. 6C), confirming previous observations (Roberson et al., 2012).

Similar results were obtained by indirect immunofluorescence analysis, using as a model the PR8 influenza virus. A546 cell monolayers were transfected with siPDIA3 or scRNA control as described above. After 48 h, cells were infected with PR8 IAV (5 PFU/cell) or mock-infected. In a parallel experiment, A549 cells were infected with PR8 IAV (5 PFU/cell) or mock-infected, and treated with NTZ (5 µg/ml) or vehicle immediately after the virus adsorption period. At 6 h p.i., the presence of plasma membrane-incorporated HA was determined by indirect immunofluorescence in non-permeabilized cells.

As shown in FIG. 7, much lower levels of plasma membrane-incorporated HA were detected in PDIA3-silenced cells as compared to control, indicating that PDIA3-silencing results in impairing HA transport to the cell plasma membrane, mimicking the effect of NTZ treatment (FIG. 8). Altogether these results not only confirm that PDIA3 is essential for HA protein maturation, but also demonstrate that PDIA3 down-regulation leads to a reduction of viral progeny production.

CONCLUSIONS

The PLA colocalization studies described in the present report indicate that, in the presence of NTZ, PDIA3 stably binds to the HA protein in the endoplasmic reticulum. It was also shown that NTZ directly inhibits PDIA3 disulfide-isomerase activity in an in vitro assay. NTZ-mediated PDIA3 inhibition could in turn impair the correct folding of the HA protein in the endoplasmic reticulum and prevent its trafficking to the host cell plasma-membrane.

Interestingly, it was found that PDIA3 silencing by itself mimics NTZ treatment, resulting in greatly reducing influenza HA plasma membrane levels in human A549 lung cells infected with two different influenza A virus strains.

In addition to impairing HA transport to the cell plasma-membrane, it was demonstrated that PDIA3 silencing by itself leads to a reduction of viral progeny production, suggesting that PDIA3 may represent a novel target for anti-influenza drugs.

In conclusion, on the basis of the results described in the present report, it was found that NTZ inhibits the disulfide isomerase activity of PDIA3, impairing the correct folding of the HA protein and consequently its trafficking to the plasma-membrane, a key step for correct assembly and exit of the virus from the host cell. Targeting the maturation of the viral hemagglutinin offers the opportunity to disrupt the production of infectious viral particles attacking the pathogen at a level different than the currently available anti-influenza drugs.

REFERENCES

Bernasconi, D., Amici, C., La Frazia, S., Ianaro, A., and Santoro, M. G. (2005) *J. Biol. Chem.* 280, 24127-24134.

Belardo, G., La Frazia, S., Rossignol, J. F., and Santoro, M. G. (2015) *Antimicrob. Agents Chemother.* 59, 1061-1069.

Caselli, E., Fiorentini S., Amici, C., Di Luca, D., Caruso, A., and Santoro, M. G. (2007) *Blood* 109, 2718-2726.

Di Santo N., and Ehrisman J. (2013) *Cancers* 5, 1163-1176.

Glaser, L., Conenello, G., Paulson, J., and Palese, P. (2007) *Virus Res.* 126, 9-18.

Hebert, D. N., Foellmer, B., and Helenius, A. (1995) *Cell* 81, 425-433.

Hebert D. N., and Molinari, M. (2007) *Physiol. Rev.* 87, 1377-1408.

Kreitzer, G., Schmoranzer, J., Hui Low, S., Li, X., Gan, Y., Weimbs, T., Simon, S. M., and Rodriguez-Boulan, E. (2003) *Nat. Cell. Biol.* 5, 126-136.

La Frazia, S., Amici, C., and Santoro, M. G. (2006) *Antivir. Ther.* 11, 995-1004.

La Frazia, S., Piacentini, S., Rossignol J. F., and Santoro, M. G. (2016) submitted.

Mishin, V. P., Novikok, D., Hayden, F. G., and Gubareva, L. V. (2005) *J. Virol.* 79, 12416-12424.

Molinari, M., Eriksson, K. K., Calanca, V., Galli, C., Cresswell, P., Michalak, M., and Helenius, A. (2004). *Mol. Cell* 13, 125-135.

Muller J., Naguleswaran A., Muller N., and Hemphill, A. (2008) *Exp. Parasitol.* 118, 80-88.

Ohuchi, R., Ohuchi, M., Garten, W., and Klenk, H. D. (1997) *J. Virol.* 71, 3719-3725.

Piacentini, S., La Frazia, S., Rossignol J. F. and Santoro M. G. (2015) *4th ISIRV AVG Conference Abstracts*, Jun. 2-4, 2015, Austin, Tex., USA Pica, F., Palamara, A. T., Rossi, A., De Marco, A., Amici, C., and Santoro, M. G. (2000) *Antimicrob. Agents Chemother.* 44, 200-204.

Roberson E. C., Tully J. E., Guala A. S., Reiss J. N., Godburn K. E., Pociask D. A., Alcorn J. F., Riches D. W. H., Dienz O., Janssen-Heininger Y. M. W., and Anathy V. (2012). Am. J. Respir. Cell. Mol. Biol. 46, 573-581.

Rossi, A., Kapahi, P., Natoli, G., Takahashi, T., Chen, Y., Karin, M., and Santoro, M. G. (2000) *Nature* 403, 103-108.

Rossignol, J. F., La Frazia, S., Chiappa, L., Ciucci, A., Santoro, M. G. (2009) *J. Biol. Chem.* 284, 29798-29808.

Sarge, K. D, Murphy, S. P., and Morimoto, R. I. (1993) *Mol. Cell. Biol.* 13, 1392-1407.

Soldà T., Garbi N., Hammerling G. J., and Molinari M. (2006) *J. Biol. Chem.* 281, 6219-6226.

Tatu, U., Hammond, C., and Helenius, A. (1995) *EMBO J.* 14, 1340-1348.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of treating a disease or condition associated with an increased level of expression of protein disulfide-isomerase A3 comprising administering to a subject in need thereof a protein disulfide-isomerase A3-inhibiting effective amount of a pharmaceutical composition comprising at least one thiazolide compound, wherein the at least one thiazolide compound comprises (a) nitazoxanide or a pharmaceutically acceptable salt thereof, (b) tizoxanide or a pharmaceutically acceptable salt thereof or (c) a combination thereof, wherein the at least one thiazolide compound inhibits protein disulfide isomerase A3 more than it inhibits other protein disulfide isomerases, and wherein the disease or condition is a liver fibrosis or a renal fibrosis.

2. The method of claim 1, wherein the thiazolide compound is nitazoxanide, tizoxanide, or a pharmaceutically acceptable salt thereof.

3. The method of claim 1, wherein the pharmaceutical composition comprises nitazoxanide or a pharmaceutically acceptable salt thereof.

4. The method of claim 1, wherein the pharmaceutical composition comprises tizoxanide or a pharmaceutically acceptable salt thereof.

5. The method of claim 1, wherein the pharmaceutical composition comprises nitazoxanide and tizoxanide.

6. The method of claim 1, wherein the disease or condition is a renal fibrosis.

7. The method of claim 1, wherein the subject is a human being.

8. The method of claim 1, wherein the disease or condition is a liver fibrosis.

* * * * *

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tccagccaac aagaagctaa a                                              21